United States Patent [19]

Lagow et al.

[11] Patent Number: 4,510,335
[45] Date of Patent: Apr. 9, 1985

[54] PERFLUORINATED BRANCHED ETHER COMPOUNDS

[76] Inventors: Richard J. Lagow, 6204 Shadow Mountain, Austin, Tex. 78731; Daniel F. Persico, 908 Hermitage Dr., Austin, Tex. 78753

[21] Appl. No.: 363,113

[22] Filed: Mar. 29, 1982

[51] Int. Cl.$^3$ .................... C07C 43/12; B01J 13/00
[52] U.S. Cl. ............................. 568/683; 252/311; 252/312
[58] Field of Search ............... 568/683, 682, 698; 252/311, 312

[56] References Cited

U.S. PATENT DOCUMENTS

| | | | |
|---|---|---|---|
| 2,500,388 | 3/1950 | Simons | 568/683 |
| 4,187,252 | 2/1980 | Lagow et al. | 260/653 |
| 4,281,119 | 7/1981 | Lagow et al. | 544/106 |

OTHER PUBLICATIONS

Chemical Abstracts, vol. 77, 1972, p. 397, Abst. No. 87786, "Splitting of Perfluoroisobutylene Oxide by Perfluoroalkoxy Anions".

Primary Examiner—Richard D. Lovering
Assistant Examiner—Anne Brookes
Attorney, Agent, or Firm—Hamilton, Brook, Smith and Reynolds

[57] ABSTRACT

This invention relates to perfluorinated branched ether compounds which are useful as synthetic blood substitutes and perfusion media, and for other purposes, and to emulsions which contain such compounds. A method is disclosed for direct fluorination without creating excessive unwanted byproducts. Hydrocarbon ether starting compounds used in this invention may be purchased or synthesized.

5 Claims, 1 Drawing Figure

PERFLUORINATED BRANCHED ETHER COMPOUNDS

GOVERNMENT SUPPORT

The invention described herein was supported in whole or in part by the United States Air Force Office of Scientific Research.

TECHNICAL FIELD

This invention is in the fields of chemistry and biology, and more particularly fluorocarbon chemistry and blood substitutes.

BACKGROUND ART

Several synthetic fluorocarbon compounds are known to be useful as blood substitutes. Such compounds are described in U.S. Pat. No. 3,911,138 (Clark, 1975), which describes emulsions that contain perfluorinated cyclic hydrocarbons, and U.S. Pat. Nos. 4,110,474 and 4,187,252 (Lagow et al, 1978 and 1980), which describe emulsions that contain perfluorotetramethyl pentane. However, continuing work is being done to create and identify other compounds which are also suitable as blood substitutes, perfusion media, breathable liquids, and for other biological and chemical purposes. Such compounds are likely to have superior qualities regarding one or more relevant characteristics, which include: oxygen affinity and release, solubility or emulsifiability in various media, low toxicity, high shelf life, appropriate stability within the body, low retention within vital organs of the body, and low cost of manufacture.

As used herein, the prefix "perfluoro-" and the term "perfluorinated" indicate that all or essentially all of the replaceable atoms (such as hydrogen) in a compound have been replaced by fluorine atoms. As used herein, the term "hydrocarbon" refers to molecules that contain hydrogen and carbon atoms, regardless of whether they also contain oxygen, fluorine or other atoms.

DISCLOSURE OF THE INVENTION

This invention relates to novel organic compounds which are useful as synthetic blood substitutes and perfusion media, and for other purposes. This invention also relates to emulsions and other mixtures which contain such compounds, and to processes for preparing such compounds.

More particularly, this invention relates to perfluorinated branched ether compounds, which have the following general formula:

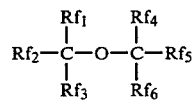

where $Rf_1$ through $Rf_6$ represent perfluorinated organic moieties or fluorine atoms. The concept of "branched," which is well understood in the art, indicates that not all of the carbon atoms in a molecule occur in a continuous (sometimes called normal or linear) sequence. For example, neopentane

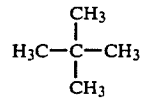

and isopentane

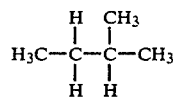

are branched, while n-pentane

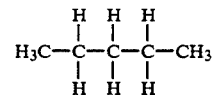

is not branched.

The compounds created by the methods of this invention include the following structures:

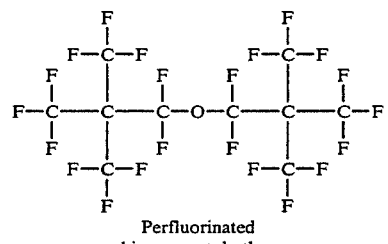

Perfluorinated bis-neopentyl ether

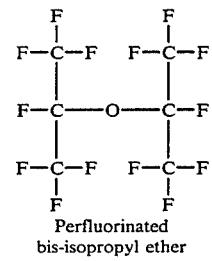

Perfluorinated bis-isopropyl ether

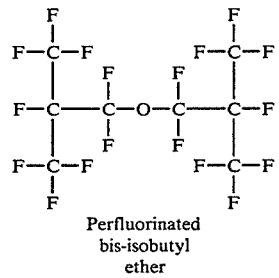

Perfluorinated bis-isobutyl ether

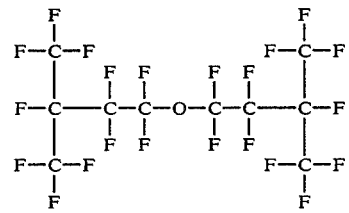

Perfluorinated bis-isopentyl ether

Perfluorinated bis-tertiary-butyl ether

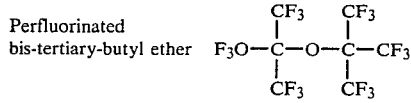

The method of this invention comprises at least two steps, and preferably includes at least one additional step of purification. The first step comprises obtaining, by synthesis or by selection, a branched hydrocarbon ether compound with carbon and oxygen atoms in the desired configuration. If the hydrocarbon ether thus obtained contains significant quantities of impurities, byproducts, or other undesired compounds, then a purification step may be preferred. A necessary third step involves perfluorinating the hydrocarbon ether compound. If desired, another purification step may be performed after perfluorination. If desired, the resulting perfluorinated branched ether may be mixed with solvents, saline solutions or aqueous solutions, or other fluids to increase its usefulness as a blood substitutes, perfusion media, or breathable liquid, or for other biological or chemical purposes.

The products described herein have been created and analyzed by chemical techniques. Although biological testing is not yet complete, it is believed that these compounds are relatively nontoxic and useful as blood substitutes.

BEST MODE OF CARRYING OUT THE INVENTION

Figure 1:
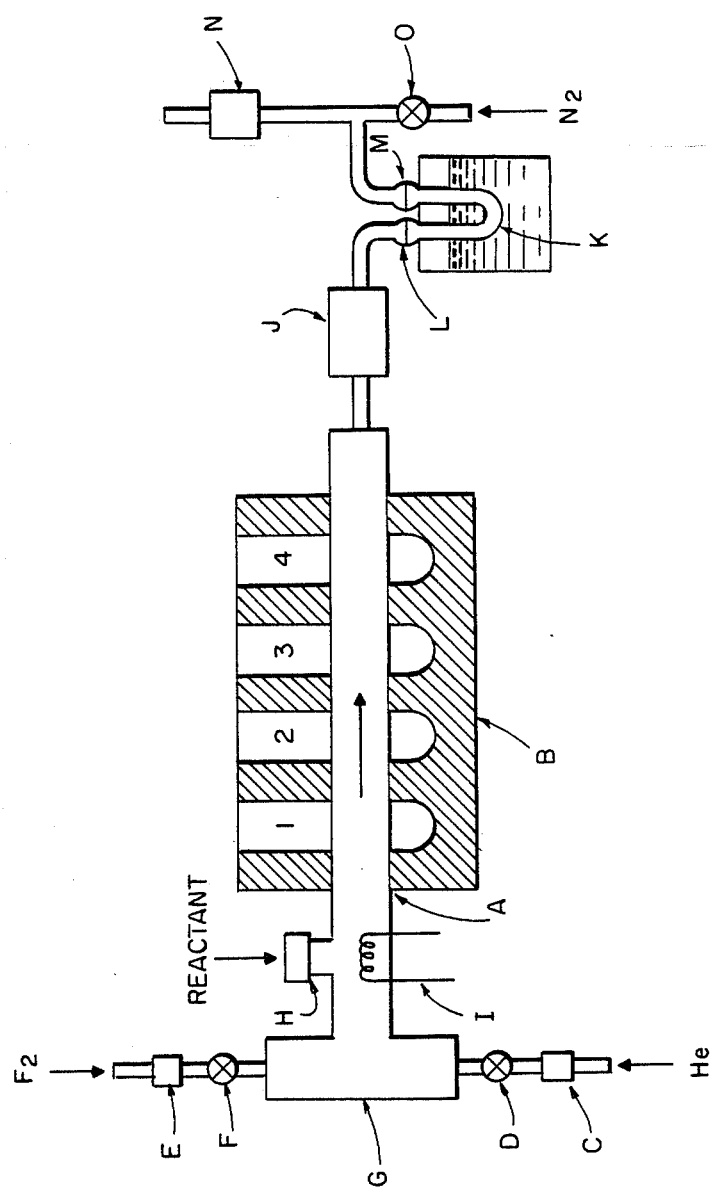
FIG. 1 is a simplified representation of a multizone perfluorination system.

One preferred mode of carrying out the method of this invention involves the perfluorination of selected branched hydrocarbon ether compounds which are commercially available. Such hydrocarbon compounds include bis-isopropyl ether, bis-isobutyl ether, and bis-isopentyl ether. Such compounds may be purchased with sufficiently high degrees of purity to render it unnecessary to purify them further before the perfluorination reaction.

An alternate preferred method of this invention involves the perfluorination of branched hydrocarbon ether compounds which are not readily commercially available, such as bis-neopentyl ether. Such compounds may be synthesized. One reaction which is suitable for creating certain ether compounds involves reacting a branched tosylate compound with the salt of an alcohol, according to the following formula:

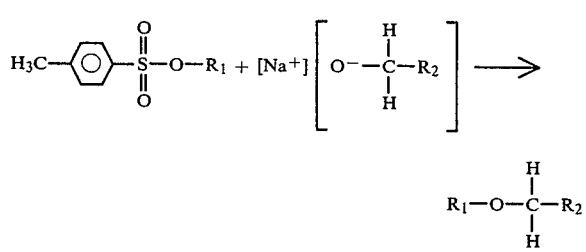

where $R_1$ and $R_2$ represent branched hydrocarbon groups. Several versions of this reaction involving specific compounds have been published.

If desired, a synthesized or selected branched hydrocarbon ether compound may be purified. If the relevant properties of the ether compound are known or can be determined, purification to an economically optimal degree can usually be accomplished by those skilled in the art by means of conventional techniques, including various types of distillation and chromatography.

An essential step of this invention comprises perfluorinating the branched hydrocarbon ether compound. This may be done by careful application of direct fluorination in a multi-zone cooled reactor system. Direct fluorination of hydrocarbons is a very exothermic reaction, and care must be taken to avoid fragmenting the molecules being fluorinated. To reduce fragmentation, fluorine is introduced slowly and at low temperatures. This procedure can be briefly summarized as follows, using a typical reaction system as shown in FIG. 1. This type of system is described in U.S. Pat. No. 4,113,435; 4,187,252; and 4,281,119 (Lagow et al).

Part A of FIG. 1 is the main reaction chamber. It consists of a cylinder made of nickel, Monel alloy, or other material which resists fluorine attack. It may be packed with copper turnings to provide an extensive internal surface area for condensation of gases or other reactants. It passes through insulating block B, which has had four wells, designated as 1, 2, 3, and 4, cut into it. When a cold substance such as liquid nitrogen (which vaporizes at $-196°$ C.) is poured into well 1, it cools that region of the reactor zone to approximately the same temperature as the liquid. Each well can be filled with a different cold substance, allowing the temperature of each zone to be controlled independently of the other zones. If desired, each well may be temperature-controlled by an automatic device. For example, a thermocouple may be placed on the reactor surface in each well. Depending on the temperature in the well, it will generate an electric signal which can be processed and used to control the rate of flow of a cold substance into the well.

An inert gas such as helium is used to flush all oxygen and other reactive molecules out of reaction chamber A before the reaction begins. The helium enters the chamber through flow meter C (for example, Metheson Gas Model 600 flowmeter) and metering valve D. After the chamber is thoroughly flushed, the helium flow is stabilized, and one or more of the reactor zones are cooled by adding cold substances to one or more of wells 1 through 4. The material to be fluorinated (hereafter called the reactant) is injected into the system through fitting H. Certain reactants may be injected in gaseous form; other reactants may be injected in liquid form, volatilized by heating coil I, and caused to condense on the surfaces of the copper turnings inside reaction Chamber A. Alternately, if the reactant is a solid or liquid, it may be loaded into a small, shallow tray often called a "boat," and set inside the reaction vessel; in this case, the copper turnings may be removed from the reaction chamber.

After the chamber has been flushed with helium, cooled, and loaded with reactant, then fluorine is added to the chamber by means of flowmeter E (for example, Hastings Model LF50X flowmeter) and metering valve F. The helium and fluorine mix together in mixing chamber G before they contact the reactant. The fluorine flow is increased in a stepwise or gradual manner and the helium flow is decreased, until concentrated or pure fluorine is flowing through chamber A. If desired, the temperature of the chamber may be elevated by placing hot liquid in one or more of wells 1 through 4. If desired, the system can be designed to accommodate elevated pressures.

When the fluorination reaction is complete, the fluorine flow is terminated and chamber A is flushed with helium if desired. Chamber A is then warmed to a desired temperature, which increases the volatility of the perfluorinated compound. The compound vaporizes and is removed from chamber A by the continuing helium flow. The system may be fitted with a trap J, which may be filled with a substance such as sodium fluoride (NaF) to remove HF from the exiting stream.

The exiting gas stream passes through condensation trap K. When volatile perfluorinated compounds are leaving chamber A, trap K is immersed within a cold liquid, such as liquid nitrogen or a dry ice-isopropanol slush, to chill the trap. The compounds condense within the trap, which can be removed from the system by means of fittings L and M.

The system may be fitted with a trap N, containing an adsorbent compound such as alumina ($Al_2O_3$) to remove unreacted fluorine. The system may also be equipped with means for insuring that oxygen does not enter the system, such as a valve O to allow an inert gas such as nitrogen to enter the system at a slight pressure. The gas which exits trap N may travel through a substance such as mineral oil, which turns black if the gas contains fluorine; this indicates that the alumina in trap N should be replaced.

The fourth and final step of the reaction comprises purifying the perfluoroether. After the characteristics of the compound have been determined, the purification step can often be performed using conventional means, such as distillation or gas chromatography.

EXAMPLE 1

F-bis-neopentyl ether

Unfluorinated bis-neopentyl ether was synthesized by a method described by V. Gosh, J. Org. Chem. 37 No. 13, p.(1972). A brief summary of that process follows. 0.23 mole (20 g) of neopentyl alcohol (Aldrich Chemical Co., Milwaukee, WI) was dissolved in 150 ml of reagent grade toluene. A stoichiometric amount (5.3 g) of elemental sodium was added. The mixture was stirred and refluxed at a temperature slightly above the boiling point of toluene (109° C.) until all of the metallic sodium had been dissolved, according to the following reaction:

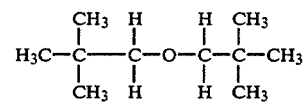

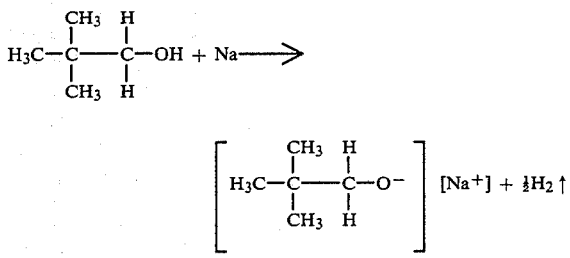

In a separate vessel, neopentyl alcohol and p-toluenesulfonyl chloride (Matheson, Coleman & Bell, Cincinnati, OH) were reacted in toluene to form neopentyl tosylate, according to the following reaction:

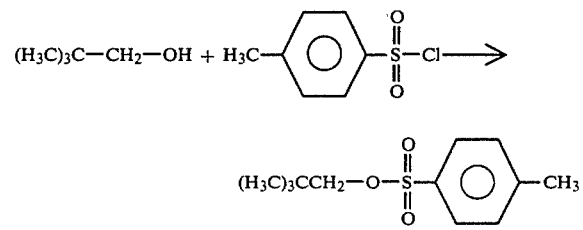

0.23 mole (56 g) of neopentyl tosylate, dissolved in toluene, was added to the first solution. The mixture was refluxed for seven days to create bis-neopentyl ether, which has the following structure, $$H_3C-\underset{\underset{CH_3}{|}}{\overset{\overset{CH_3}{|}}{C}}-\underset{\underset{H}{|}}{\overset{\overset{H}{|}}{C}}-O-\underset{\underset{H}{|}}{\overset{\overset{H}{|}}{C}}-\underset{\underset{CH_3}{|}}{\overset{\overset{CH_3}{|}}{C}}-CH_3$$

along with a variety of byproducts.

The bis-neopentyl ether was purified by the following method. All volatile products were vacuum distilled from the reflux chamber by using a vacuum of about $10^{-3}$ torr absolute pressure. They were collected in a trap cooled to about $-196°$ C. by liquid nitrogen. The collected products were allowed to warm to room temperature, and were then heated to conduct a fractional distillation. A crude cut was collected which boiled in the temperature range of 122° to 129° C. This cut was then distilled again, and a refined cut was collected in the range of 127° to 129° C. This cut was analyzed by gas chromatography, which indicated that it was bis-neopentyl ether with a purity of about 90 to 95%.

A multi-zone reaction vessel filled with copper turnings was flushed with helium. Various zones were chilled to about $-80°$ C. by placing dry ice in several wells that surrounded the reactor cylinder. Bis-neopentyl ether was injected into the system, and vaporized by a heating coil. It was carried by helium flow to the chilled copper turnings, where it condensed. Fluorine and helium were passed through the reaction chamber according to the rates specified in Table 1. The fluorine content was gradually increased and the helium flow was decreased until relatively pure fluorine was contacting the ether. After the fluorination reaction had proceeded for an appropriate period, the fluorine flow was discontinued and helium flow was commenced. The reaction chamber was then warmed to room temperature to cause the F-bis-neopentyl ether (which is a solid below about 68° C.) to sublime. The vapor was carried out of the chamber by the helium flow and collected in a trap cooled by dry ice. It was purified by gas chromatography, and analyzed to provide the following results.

$^{19}F$ NMR (nuclear magnetic resonance) consisted of a pentet (a multiplet of five) at $-64.2$ ppm downfield from an internal standard of $CFCl_3$, corresponding to the $CF_3$ groups. The $^{19}F$ NMR also exhibited a multiplet of 10 centered at $-67.5$ in relation to $CFCl_3$, corresponding to the $CF_2$ groups. The relative ratio from integrating the area under the resonances was a ratio of 4.3 to 1, compared to an expected ratio of 4.5 to 1. The mass spectrum contained peaks that were regarded as appropriate. The peak at the highest m/e (at 497) corresponded to the molecular weight of the compound with three fluorine atoms removed.

TABLE 1

| REACTION CONDITIONS: bis-neopentyl ether | | | | | | |
|---|---|---|---|---|---|---|
| TIME | HELIUM | F$_2$ | ZONES & TEMP. (°C.)* | | | |
| HOURS | cc/min. | cc/min. | 1 | 2 | 3 | 4 |
| 12 | 30 | 2.5 | −80 | −80 | −80 | −80 |
| 12 | 15 | 2.5 | −80 | −80 | −80 | −80 |
| 12 | 5 | 2.5 | RT | −80 | −80 | −80 |
| 12 | 0 | 1.0 | RT | −80 | −80 | −80 |
| 12 | 0 | 2.0 | RT | RT | −80 | −80 |
| 12 | 20 | 2.0 | RT | RT | RT | −80 |
| 12 | 60 | 0 | RT | RT | RT | RT |

*RT = Room Temperature

TABLE 2

PERFLUORO-BIS-NEOPENTYL ETHER $$(CH_3)_3CCH_2OCH_2C(CH_3)_3 \xrightarrow[-78°C.-RT]{F_2} (CF_3)_3CCF_2OCF_2C(CF_3)_3$$

M.P. 68–68.5° C.
$^{19}$F NMR: (CF$_3$Cl INTERNAL STANDARD)
[(CF$_3$)$_3$C—CF$_2$—]$_2$O    J = 5.58 Hz
−64.2  −67.5

RATIO OF INTENSITIES

Theoretical—4:5:1,
Actual—4:5:1.

MASS SPECTRUM 535 (P-F), 497 (P-F$_3$), 269 [(CF$_3$)CCF$_2$] Base peak in spectrum, 219 [(CF$_3$)$_3$C], 69 (CF$_3$).

IR cm$^{-1}$ 1270 (vs, br), 1220 (s), 1085 (s, sh), 988 (s), 729 (m)

GC Separation using ⅜"×25' column with 10% fluorosilicone QF-1-0065 on Chromasorb P. Retention time at 45° C. is 16 minutes, 15 seconds at 100 cc/min. He flow.

EXAMPLE 2

Perfluorinated bis-isopropyl ether

Unfluorinated bis-isopropyl ether was purchased from Aldrich Chemical Co., Milwaukee WI. It was perfluorinated by the method described in Example 1, using the helium and fluorine gas flows and temperatures specified in Table 1—1. The results of a product analysis are in Table 2-1.

TABLE 1-1

| ISOPROPYL ETHER FLUORINATION CONDITIONS | | | | | | | | | |
|---|---|---|---|---|---|---|---|---|---|
| Hours | He | F$_2$ | 1 | 2 | 3 | 4 | 5 | 6 | 7 | 8 |
| 12 | 40 | 0.5 | −78 | −90 | −90 | | | | | |
| 12 | 20 | 0.5 | | −78 | −78 | −78 | | | | |
| 12 | 20 | 1.0 | −78 | −78 | −78 | −78 | | | | |
| 12 | 10 | 1.0 | | −78 | −78 | −78 | −78 | | | |
| 12 | 10 | 2.0 | | | −78 | −78 | −78 | −78 | | |
| 12 | 5 | 2.0 | | | | −78 | −78 | −78 | −78 | |
| 12 | 5 | 4.0 | | | | | −78 | −78 | −78 | |

TABLE 1-1-continued

| ISOPROPYL ETHER FLUORINATION CONDITIONS | | | | | | | | | |
|---|---|---|---|---|---|---|---|---|---|
| Hours | He | F$_2$ | 1 | 2 | 3 | 4 | 5 | 6 | 7 | 8 |
| 12 | 0 | 1.0 | | | | | | | −78 | −78 |
| 12 | 0 | 2.0 | | | | | | | −78 | −78 |
| 12 | 0 | 2.0 | | | | | | | | −78 |
| 12 | 0 | 2.0 | | | | | | | | RT |
| 12 | 60 | 0 | | | | | | | | RT |

TABLE 2-1

PERFLUORO-BIS-ISOPROPYL ETHER $$(CH_3)_2CHOCH(CH_3)_2 \xrightarrow[-90°-RT]{F_2} (CF_3)_2CFOCF(CF_3)_2$$

$^{19}$F NMR: (CFCl$_3$ INTERNAL STANDARD)
[(CF$_3$)$_2$—CF—]$_2$O    J = 5.07 Hz
−83.0  −143.0

RATIO OF INTENSITIES

Theoretical—6:1,
Actual—6:1.

MASS SPECTRUM 335 (P-F), 285 (P-CF$_3$), 235 (P-C$_2$F$_5$).
169 [(CF$_3$)$_2$CF] Base Peak, 69(CF$_3$).

IR cm$^{-1}$ 1362 (m), 1290 (s), 1230 (s, br), 1130 (s, br), 992 (m),

GC Separation using ⅜"×25' column with 10% fluorosilicone QF-1-0065 on Chromosorb P. Retention time at 0° C. is 7 minutes, 30 seconds at 100 cc/min. He flow.

EXAMPLE 3

Perfluorinated bis-isobutyl ether

Unfluorinated bis-isobutyl ether was purchased from Tridom-Fluka AG, Hauppauge, NY. It was perfluorinated by the method described in Example 1, using the helium and fluorine gas flows and temperatures specified in Table 3. The results of a product analysis are in Table 4.

TABLE 3

| REACTION CONDITIONS: bis-isobutyl ether | | | | | | |
|---|---|---|---|---|---|---|
| TIME | HELIUM | F$_2$ | ZONES & TEMP. (°C.)* | | | |
| HOURS | cc/min. | cc/min. | 1 | 2 | 3 | 4 |
| 12 | 20 | 0.5 | −80 | −80 | −80 | −80 |
| 12 | 20 | 1.5 | −80 | −80 | −80 | −80 |
| 24 | 20 | 1.5 | RT | −80 | −80 | −80 |
| 12 | 10 | 2.0 | RT | −80 | −80 | −80 |
| 24 | 5 | 3.0 | RT | RT | −80 | −80 |
| 12 | 0 | 2.0 | RT | RT | −80 | −80 |
| 12 | 0 | 3.0 | RT | RT | RT | −80 |
| 12 | 0 | 3.0 | RT | RT | RT | RT |

*RT = Room Temperature

TABLE 4

$$(CH_3)_2CHCH_2OCH_2CH(CH_3)_2 \xrightarrow[-90°C.-RT]{F_2} (CF_3)_2CFCF_2OCF_2CF(CF_3)_2$$

$^{19}$F NMR: (CFCl$_3$ EXTERNAL STANDARD, NEAT SAMPLE)
[(CF$_3$)$_2$—CF—CF$_2$—]$_2$O    CF RESONANCE NOT OBSERVED
−75.5  −78.2

RATIO OF INTENSITIES

Theoretical—6:1:2
Actual—6: :2

CF RESONANCE NOT OBSERVED

MASS SPECTRUM 435 (P-F), 397 (P-F$_3$), 366 (P-CF$_4$),
219 [(CF$_3$)$_2$CFCF$_2$]Base Peak, 69 (CF$_3$).

IR cm$^{-1}$ 1270 (vs, br), 1165 (s), 990 (s), 840 (m, sh), 705 (m).

GC Separation using $\frac{3}{8}''\times 25'$ column with 10% fluorosilicone QF-1-0065 on Chromosorb P. Retention time at 30° C. is 5 minutes at 100 cc/min. He flow.

EXAMPLE 4

Perfluorinated bis-isopentyl ether

Unfluorinated isopentyl ether was purchased from Pfaultz & Bauer, Stamgord, Conn. . It was perfluorinated by the method dexcribed in Example 1, using the helium and fluorine gas flows and temperatures specified in Table 5. The results of a product analysis are in Table 6.

TABLE 5

| TIME HOURS | HELIUM cc/min. | F$_2$ cc/min. | ZONES & TEMP. (°C.)* | | | |
|---|---|---|---|---|---|---|
| | | | 1 | 2 | 3 | 4 |
| 12 | 20 | 0.5 | −80 | −80 | −80 | −80 |
| 12 | 20 | 1.5 | −80 | −80 | −80 | −80 |
| 24 | 20 | 1.5 | RT | −80 | −80 | −80 |
| 12 | 10 | 2.0 | RT | −80 | −80 | −80 |
| 24 | 5 | 3.0 | RT | RT | −80 | −80 |
| 12 | 0 | 2.0 | RT | RT | −80 | −80 |
| 12 | 0 | 3.0 | RT | RT | RT | −80 |
| 12 | 0 | 3.0 | RT | RT | RT | RT |

*RT = Room Temperature

TABLE 6

PERFLUORO-BIS-ISOPENTYL ETHER

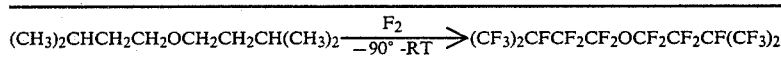

$(CH_3)_2CHCH_2CH_2OCH_2CH_2CH(CH_3)_2 \xrightarrow[-90°\text{-RT}]{F_2} (CF_3)_2CFCF_2CF_2OCF_2CF_2CF(CF_3)_2$ $^{19}$F NMR: (CFCl$_3$ EXTERNAL STANDARD, NEAT SAMPLE)
[(CF$_3$)$_2$—CF—CF$_2$—CF$_2$—]$_2$O
 −74.0 −120 −84.4

CF RESONANCE NOT OBSERVED

RATIO OF INTENSITIES

Theoretical—6:1:2:2,
Actual—6: :2:2.

MASS SPECTRUM 535 (P-F), 497 (P-F$_3$), 269 [(CF$_3$)$_2$CFCF$_2$CF$_2$]
Base Peak, 219 [(CF$_3$)$_2$CF CF$_2$], 69 (CF$_3$)

IR cm$^{-1}$ 1250 (vs, br), 1150 (m), 982 (m,sh), 880 (w), 722 (m)

GC Separation on $\frac{3}{8}''\times 25'$ column with 10% fluorosilicone QF-1-0065 on Chromosorb P. Retention time at 40° C. is 21 minutes, 15 seconds at 100 cc/min. He flow.

EXAMPLE 5

F-bis-tertiary-butyl ether

Unfluorinated bis-tertiary-butyl ether was synthesized by a method described by J. L. E. Erickson & William H. Ashton. J. Am. Chem. Soc., 63, p1769(1941). A brief summary of that process follows. Silver Carbonate (Aldrich Chemical Co., Milwaukee WI) 0.5 moles (137 grams) in 400 mls of diethyl ether was combined with tertiary-butyl chloride (Eastman Organic Co., Rochester. NY) 1.0 moles (93 grams) and brought to 0° C. This solution, in the exclusion of light, was stirred for 24 hours. After this, the ether layer was decanted and distilled and the bis-tertiary ether, (bp 106° C.) was separated from the diethyl ether, (bp 32° C.). The bis-tertiary butyl ether was then distilled over sodium to assure dryness. It was perfluorinated by the method described in Example 1 using the helium and fluorine gas flows and temperatures specified in Table 7. The results of a product analysis are in Table-8

TABLE 7

| REACTION CONDITIONS: bis-tertiary-butyl ether | | | | | | |
|---|---|---|---|---|---|---|
| Time Hours | Helium cc/min | F$_2$ cc/min | Zones & Temp (°C.)* | | | |
| | | | 1 | 2 | 3 | 4 |
| 12 | 30 | 1.0 | −78 | −100 | −100 | −78 |
| 24 | 30 | 2.0 | RT | −78 | −100 | −100 |
| 12 | 15 | 2.0 | RT | −78 | −100 | −100 |
| 12 | 15 | 3.0 | RT | RT | −78 | −100 |
| 24 | 5 | 3.0 | RT | RT | −78 | −100 |
| 12 | 0 | 2.0 | RT | RT | RT | −100 |
| 12 | 0 | 3.0 | RT | RT | RT | −78 |
| 12 | 0 | 3.0 | RT | RT | RT | RT |
| 12 | 60 | 0 | RT | RT | RT | RT |

*RT = Room Temperature

TABLE 8

PERFLUORO-BIS-TERTIARY-BUTYL ETHER $(CH_3)_3COC(CH_3)_3 \xrightarrow[-100\text{-RT}]{F_2} (CF_3)_3COC(CF_3)_3$ $^{19}$F NMR (CFCl$_3$ INTERNAL STANDARD)
[(CF$_3$)$_3$C]$_2$O
 −62.5

MASS SPECTRUM

435(P-F), 397(P-F$_3$), 385(P-CF$_3$)
219((CF$_3$)$_3$C) Base Peak, 69(CF$_3$.

IR cm$^{-1}$

1260(vs,br), 1170(s), 985(m), 730(m),

GC. Seperation on $\frac{3}{8}''\times 25'$ column with 10% fluorosilicone QF-1-0065 on Chromosorb P.

We claim:
1. Perfluorinated bis-neopentyl ether.
2. Perfluorinated bis-isopropyl ether.
3. Perfluorinated bis-isobutyl ether.
4. Perfluorinated bis-isopentyl ether.
5. Perfluorinated bis-tertiary-butyl ether.

* * * * *